(12) United States Patent
Takada et al.

(10) Patent No.: US 6,734,214 B1
(45) Date of Patent: May 11, 2004

(54) REMEDIES FOR DIABETES

(75) Inventors: Shigeo Takada, Kanagawa (JP); Yasukazu Nagato, Kanagawa (JP); Masahiro Murakami, Osaka (JP)

(73) Assignee: Amato Pharmaceutical Products, Ltd., Kyoto (JP)

( * ) Notice: Subject to any disclaimer, the term of this patent is extended or adjusted under 35 U.S.C. 154(b) by 0 days.

(21) Appl. No.: 10/030,170

(22) PCT Filed: Aug. 9, 2000

(86) PCT No.: PCT/IB00/01112

§ 371 (c)(1), (2), (4) Date: Apr. 22, 2002

(87) PCT Pub. No.: WO01/10451

PCT Pub. Date: Feb. 15, 2001

(30) Foreign Application Priority Data

Aug. 9, 1999 (JP) ............................................ 11/224883

(51) Int. Cl.⁷ ................................................ A61K 31/19
(52) U.S. Cl. ...................... 514/557; 514/574; 514/866
(58) Field of Search ................................ 514/557, 574, 514/866

(56) References Cited

FOREIGN PATENT DOCUMENTS

| JP | 5-310581 | 11/1993 |
| JP | 6-336427 | 12/1994 |
| JP | 7-233061 | 9/1995 |
| JP | 9-227388 | 9/1997 |
| JP | 10130153 | 5/1998 |
| JP | 2000-72680 | 3/2000 |
| JP | 2000239171 | 9/2000 |

OTHER PUBLICATIONS

English Language Abstract of–JP–2000–072680.
English Language Abstract of–JP–2000–239171.
English Language Abstract of–JP–10–130153.
English Language Abstract of–JP–9–227388.
English Language Abstract of–JP–7–233061.
English Language Abstract of–JP–6–336427.
English Language Abstract of–JP–5–310581.

*Primary Examiner*—Kevin E. Weddington
(74) *Attorney, Agent, or Firm*—Greenblum & Bernstein, P.L.C.

(57) ABSTRACT

The object of the present invention is to provide a medicament for prevention and/or treatment of diabetes or diabetes complications, which has an action of reducing the blood sugar level. The present invention provides a medicament for prevention and/or treatment of diabetes or diabetes complications which comprises, as an active ingredient, a mixture of cyclic and/or straight chain poly lactic acids having a condensation degree of 3 to 19.

25 Claims, 5 Drawing Sheets

Fig.1: Mass

Fig. 2: Effect of CPL on the fasting blood sugar level

Fig.4:

Effect of CPL on the food consumption

Fig.5:

Effect of CPL on the weight increase

REMEDIES FOR DIABETES

TECHNICAL FIELD

The present invention relates to a medicament for prevention and/or treatment of diabetes or diabetes complications, more specifically a medicament for prevention and/or treatment of diabetes or diabetes complications which comprises, as an active ingredient, a mixture of poly lactic acids having certain condensation degree.

BACKGROUND ART

Diabetes is a metabolic disorder mainly of glucose metabolism which is based on deficient secretion of insulin or reduced sensitivity of target cells thereof, and a major characteristic of diabetes is hyperglycemia. If hyperglycemia persists for a long period, serious complications such as retinopathy, nephropathy and neuropathy arise in various organs and nerves with angiopathy as a prime factor. Therefore, it is extremely important in the treatment of diabetes to control the blood sugar level and maintain it at a normal level, and the means for this purpose has been studied for many years.

Diabetes is classified according to the types of disease into insulin dependent diabetes (IDDM; type I diabetes) and non-insulin dependent diabetes (NIDDM; type II diabetes). In the case of non-insulin dependent diabetes (type II diabetes), onset of the disease is slow and insulin treatment is not necessarily required for maintaining life, and the blood sugar level can be controlled by a combination of diet therapy, kinesitherapy and drug therapy. In drug therapy, an insulin secretion promoting agent which is one type of oral agents for reducing the blood sugar level is widely and clinically used. However, since currently available insulin secretion promoting agents promote insulin secretion independent of blood sugar level, there arise problems that onset of serious hypoglycemia arises or the blood sugar level cannot be sufficiently controlled if the dosage is inadequate, and thus such agents are not satisfactory.

Therefore, if there is provided a novel medicament which can adequately control the blood sugar level and has little side effect, it is expected to be extremely useful for controlling the blood sugar level in diabetes patients.

DISCLOSURE OF THE INVENTION

An object of the present invention is to provide a medicament for prevention and/or treatment of diabetes or diabetes complications, which has an action of reducing the blood sugar level.

As a result of concentrated research to achieve the aforementioned object, the present inventors have found that the blood sugar level can be significantly reduced by administering a mixture of cyclic and/or straight chain poly lactic acids having a condensation degree of 3 to 19 to diabetes-induced model rats, thereby providing the present invention. Although it has been reported in the research up to now that a mixture of cyclic and/or straight chain poly L-lactic acids having a condensation degree of 3 to 19 is useful as an antineoplastic agent (Japanese Patent Application Laying-Open (Kokai) Nos. 9-227388 and 10-130153) and also as a QOL improving agent for cancer patients (Japanese Patent Application No. 11-39894 Specification; Bulletin of Japan Society of Clinical Oncology, Vol. 33, No.3, p. 493), the present inventors have found for the first time that it has an action of reducing the blood sugar level.

Thus, according to the first aspect of the present invention, there is provided a medicament for prevention and/or treatment of diabetes or diabetes complications which comprises, as an active ingredient, a mixture of cyclic and/or straight chain poly lactic acids having a condensation degree of 3 to 19.

According to another aspect of the present invention, there is provided a medicament for reducing the blood sugar level which comprises, as an active ingredient, a mixture of cyclic and/or straight chain poly lactic acids having a condensation degree of 3 to 19.

The medicament of the present invention may be used, in particular, for prevention and/or treatment of type II diabetes or complications thereof.

In a preferred embodiment of the present invention, the lactic acid which is a repeating unit in the poly lactic acid, substantially consists of L-lactic acid.

In one embodiment of the present invention, the mixture of cyclic and/or straight chain poly lactic-acids having a condensation degree of 3 to 19 that is used as an active ingredient, is a fraction obtained by condensing lactic acids (preferably lactic acid substantially consisting of L-lactic acid) by dehydration under an inactive atmosphere, subjecting the ethanol- or methanol-soluble fraction of the obtained reaction solution to reverse phase column chromatography, and eluting with 25 to 50 weight % acetonitrile aqueous solution of pH 2 to 3 and then with 90 weight % or more acetonitrile aqueous solution of pH 2 to 3.

Condensation of lactic acids by dehydration may be performed, for example, by stepwise decompression and temperature rise under a nitrogen gas atmosphere.

Moreover, reverse phase column chromatography may be performed applying ODS column chromatography.

According to another aspect of the present invention, there is provided the use of a mixture of cyclic and/or straight chain poly lactic acids having a condensation degree of 3 to 19 for the production of a medicament for prevention and/or treatment of diabetes or diabetes complications or a medicament for reducing the blood sugar level.

According to a further aspect of the present invention, there is provided a method for prevention and/or treatment of diabetes or diabetes complications or a method for reduction of the blood sugar level, which comprises a step of administering to mammals including humans, a therapeutically effective amount of a mixture of cyclic and/or straight chain poly lactic acids having a condensation degree of 3 to 19.

THE BEST MODE FOR CARRYING OUT THE INVENTION

The embodiments and methods for carrying out the present invention are described in detail below.

In the medicament of the present invention, a mixture of cyclic and/or straight chain poly lactic acids having a condensation degree of 3 to 19 is used as an active ingredient.

The term "a mixture of poly lactic acids" used in the present invention means a mixture wherein cyclic and/or straight chain poly lactic acids having a condensation degree of 3 to 19 are present at any ratio. That is to say, the term "mixture" does not only mean a mixture of poly lactic acids having any condensation degree ranging from 3 to 19, but is also used as a concept including a mixture of cyclic and straight chain poly lactic acids. As is described below in the present specification, "a mixture of poly lactic acids" can be obtained by condensing lactic acids by dehydration and then performing purification by a suitable method. Although the term "a mixture of poly lactic acids" is used in the present specification for the sake of convenience, this term also includes a poly lactic acid consisting of a single ingredient such as a cyclic poly lactic acid having single condensation degree or a straight chain poly lactic acid having single condensation degree.

The term "condensation degree" is used to mean the number of lactic acid unit which is repeating unit in poly lactic acids. For example, the cyclic poly lactic acid is assumed to have the following structural formula wherein n represents condensation degree (n=3 to 19).

When "lactic acid" is simply referred to in the present specification, this lactic acid includes all of L-lactic acid, D-lactic acid or a mixture comprising these types of lactic acid at any ratio. Preferably in the present invention, the lactic acid substantially consists of L-lactic acid. The term "substantially" is used herein to mean that the ratio of L-lactic acid units in a mixture of poly lactic acids (number of L-lactic acid unit/number of L-lactic acid unit +number of D-lactic acid unit ×100) is, for example, 70% or more, preferably 80% or more, more preferably 85% or more, further more preferably 90% or more, and particularly preferably 95% or more. The ratio of L-lactic acid units in a mixture of poly lactic acids depends on the ratio of L-lactic acid and D-lactic acid, which exist in lactic acids used as a starting substance.

Since a mixture of cyclic and/or straight chain poly lactic acids having a condensation degree of 3 to 19 shows an action of suppressing a high blood sugar level in a diabetes-induced mouse, the mixture is useful as an active ingredient in a medicament for prevention and/or treatment of diabetes or diabetes complications (e.g. retinopathy, nephropathy or neuropathy).

The methods for producing a mixture of cyclic and/or straight chain poly lactic acids having a condensation degree of 3 to 19 are not particularly limited, and the mixture of poly lactic acids can be obtained by the production methods described, for example, in Japanese Patent Application Laying-Open (Kokai) Nos. 9-227388 and 10-130153 or Japanese Patent Application No. 11-39894 (All publications cited herein are incorporated herein by reference in their entirety).

More specifically, for example, a mixture of cyclic and/or straight chain poly lactic acids having a condensation degree of 3 to 19 can be obtained by the following method.

First, lactic acid (preferably, lactic acid substantially consisting of L-lactic acid) is condensed by dehydration under an inactive atmosphere. Examples of the inactive atmosphere include nitrogen gas and argon gas, and nitrogen gas is preferred.

Dehydration and condensation reaction is carried out at a temperature of 110° C. to 210° C., preferably 130° C. to 190° C. under normal pressure or reduced pressure (about 1 mmHg), and particularly preferably the reaction is carried out by stepwise decompression and stepwise temperature rise. A reaction period can be determined as appropriate. For example, the reaction can be carried out for 1 to 20 hours. Where stepwise decompression and stepwise temperature rise are applied, the reaction period is divided into two or more partial reaction periods, and then pressure and temperature are determined for each of the reaction periods. Where stepwise decompression is applied, pressure can be reduced, for example, from a normal pressure to 150 mmHg and then to 3 mmHg. Where stepwise temperature rise is applied, temperature can be raised, for example, from 145° C. to 155° C. and then to 185° C. Practically, the reaction can be carried out by using these conditions in combination, for example, 145° C., normal pressure, 3 hours; 145° C., 150 mmHg, 3 hours; 155° C., 3 mmHg, 3 hours; and 185° C., 3 mmHg, 1.5 hours.

Subsequently, ethanol and methanol are added to the reaction mixture obtained by the dehydration and condensation reaction, and the mixture is filtered. The obtained filtrate is dried to obtain ethanol and methanol-soluble fractions. The term "ethanol and methanol-soluble fractions" is used in the present specification to mean fractions soluble in a mixed solution of ethanol and methanol. In order to obtain ethanol and methanol-soluble fractions, a reaction mixture obtained by dehydration and condensation reaction is mixed with ethanol and methanol, where the ratio of ethanol and methanol can be determined as appropriate. For example, the ratio is ethanol:methanol=1:9. The order and method for adding ethanol and methanol to a reaction mixture are not limited, and may be selected as appropriate. For example, ethanol may be added at first to the reaction mixture obtained by the dehydration and condensation reaction, and then methanol may be added thereto.

The thus obtained ethanol and methanol-soluble fractions can be subjected to reverse phase column chromatography, especially to chromatography where an octadecylsilane (ODS) column is used. First, fractions eluted with 25 to 50 weight % acetonitrile aqueous solution of pH 2 to 3 are removed, and then fractions eluted with 90 weight % or more acetonitrile aqueous solution of pH 2 to 3, preferably 99 weight % or more acetonitrile aqueous solution are collected so as to obtain a mixture of cyclic and/or straight chain poly lactic acids having a condensation degree of 3 to 19.

The obtained mixture of cyclic and/or straight chain poly lactic acids is neutralized with an alkaline substance such as sodium hydroxide, and is dried under reduced pressure, and then according to standard techniques, the mixture can be formulated in a desired forms as mentioned below.

The dosage form of the medicament of the present invention is not particularly limited, and any form suitable for the purpose of treatment or prevention can be selected from dosage forms for oral or parenteral administration. Examples of dosage forms suitable for oral administration include a tablet, a capsule, a powder, a granule, a parvule, a syrup, a solution, an emulsion, a suspension, a chewable tablet, and the like. Examples of dosage forms suitable for parenteral administration include, but are not limited to, an injection (e.g. a subcutaneous, intramuscular or intravenous injection, and the like), a drop, an inhalant, a nebula, a suppository, an agent for percutaneous absorption in the form of a gel, ointment or the like, an agent for mucomembranous absorption, and an agent for percutaneous absorption in the form of an adhesive skin patch, tape or the like.

Aqueous formulations suitable for oral administration such as a solution, emulsion or syrup can be produced using water; sugars such as sucrose, sorbit or fructose; glycols such as polyethylene glycol or propylene glycol; oils such as sesame oil, olive oil or soybean oil; antiseptics such as p-hydroxybenzoate; and flavors such as strawberry flavor and peppermint. In order to produce solid formulations such as capsule, tablet, powder or granule, there can be used an excipient such as lactose, glucose, sucrose or mannite; a disintegrator such as starch or sodium alginate; a lubricant such as magnesium stearate or talc; a binder such as polyvinyl alcohol, hydroxypropylcellulose or gelatin; a surfactant such as fatty acid ester; and a plasticizer such as glycerine, and the like.

Formulations for an injection or drop that are suitable for parenteral administration preferably comprise, as an active ingredient, the above substance in a dissolved or suspended state in a sterilized aqueous medium which is isotonic to the recipient's blood. For example, in the case of an infection, a solution can be prepared using an aqueous medium consisting of a saline solution, a glucose solution or a mixture of a saline solution and a glucose solution. In the case of a formulation for intestinal administration, it can be prepared using carriers such as a theobroma oil, hydrogenated lipids or hydrogenated carboxylic acid, and can be provided as a suppository. In order to produce a nebula, the above substance as an active ingredient may be dispersed as microparticles, and a carrier which does not irritate the recipient's cavitas oris and respiratory tract mucosa and which facilitates absorption of the active ingredient can be used. Specific examples of carriers include lactose, glycerine, and the like. Formulations having a form such as aerosol or dry powder may be prepared depending on the properties of the substance of an active ingredient and the carrier. One or two or more auxiliary ingredients selected from glycols, oils, flavors, an antiseptic, an excipient, a disintegrator, a lubricant, a binder, a surfactant, a plasticizer and the like may be added to these formulations for parenteral administration.

The dose and dosage frequency of the medicament of the present invention is determined as appropriate, depending on various factors such as the type and seriousness of the disease, dosage form, age or body weight of a patient, or the presence or absence of complications. Generally, the dose of an active ingredient per day is 20 to 2,000 mg/kg, preferably 20 to 200 mg/kg, and more preferably 50 to 150 mg/kg. It is preferred that the above dose of medicament is dividedly applied about once to 4 times per day, more preferably about twice to 4 times per day.

The medicament of the present invention can be administered to any mammal including humans, preferably being administered to humans.

The medicament of the present invention can be used for prevention and/or treatment of diabetes or diabetes complications. Diabetes is one disease, which is based on a disorder of glucose metabolism, a major characteristic of diabetes being hyperglycemia. Diabetes can be treated by reducing the blood sugar level of a diabetes patient using the medicament of the present invention. Also, diabetes can be prevented by controlling the blood sugar level of a diabetes suspected patient using the medicament of the present invention. It is known that, since hyperglycemia persists for a long period in a diabetes patient, complications such as retinopathy, nephropathy and neuropathy develop with angiopathy as a prime factor. These diabetes complications can also be prevented and/or treated by controlling the blood sugar level of a diabetes patient using the medicament of the present invention.

Moreover, the medicament of the present invention cannot only be used for prevention and/or treatment of diabetes or complications thereof, but also can broadly be used to reduce the blood sugar level. Where hyperglycemia is clinically present, diabetes is suspected, but hyperglycemia may sometimes occur due to various diseases other than diabetes. For example, hyperglycemia occurs due to various factors such as organic disorder of pancreatic tissues, chronic hepatopathy, endocrinopathy, symptom of brain hypertension, adiposis, hyperphagia, crapula of alcohol, postgastrectomy nutritional hyperglycemia, fibrile disease, carbon monoxide poisoning, increase of blood sugar due to drugs, and the like. The medicament of the present invention may be used to reduce these high level of blood sugar.

The present invention is further described in the following examples, but the examples are not intended to limit the scope of the present invention.

EXAMPLES

Production Example 1

Production of a Mixture of Poly Lactic Acids 500 ml of L-lactic acid (to which D-lactic acid is also mixed) was placed into a separable flask in a mantle heater. 300 ml/min of nitrogen gas was flowed therein while stirring. Accumulated water was introduced into a flask equipped with a reflux condenser via a warmed descending type connecting tube, while heating at 145° C. for 3 hours. Furthermore, after pressure was reduced to 150 mmHg and heated at the same temperature for 3 hours, the mixture was heated at 155° C. for 3 hours under a reduced pressure of 3 mmHg, and then at 185° C. for 1.5 hours under a reduced pressure of 3 mmHg to obtain poly lactic acids as a reaction product.

The obtained poly lactic acids were kept at 100° C., and 100 ml of ethanol and 400 ml of methanol were separately added thereto, and then the mixture was allowed to be cooled. This mixture was added to 500 ml of methanol, and the mixture was well stirred and left to stand. Then, the mixture was filtrated for purification. The filtrate was subjected to vacuum drying and then dissolved in acetonitrile to obtain 200 ml (stock solution) in total.

Figure 1:
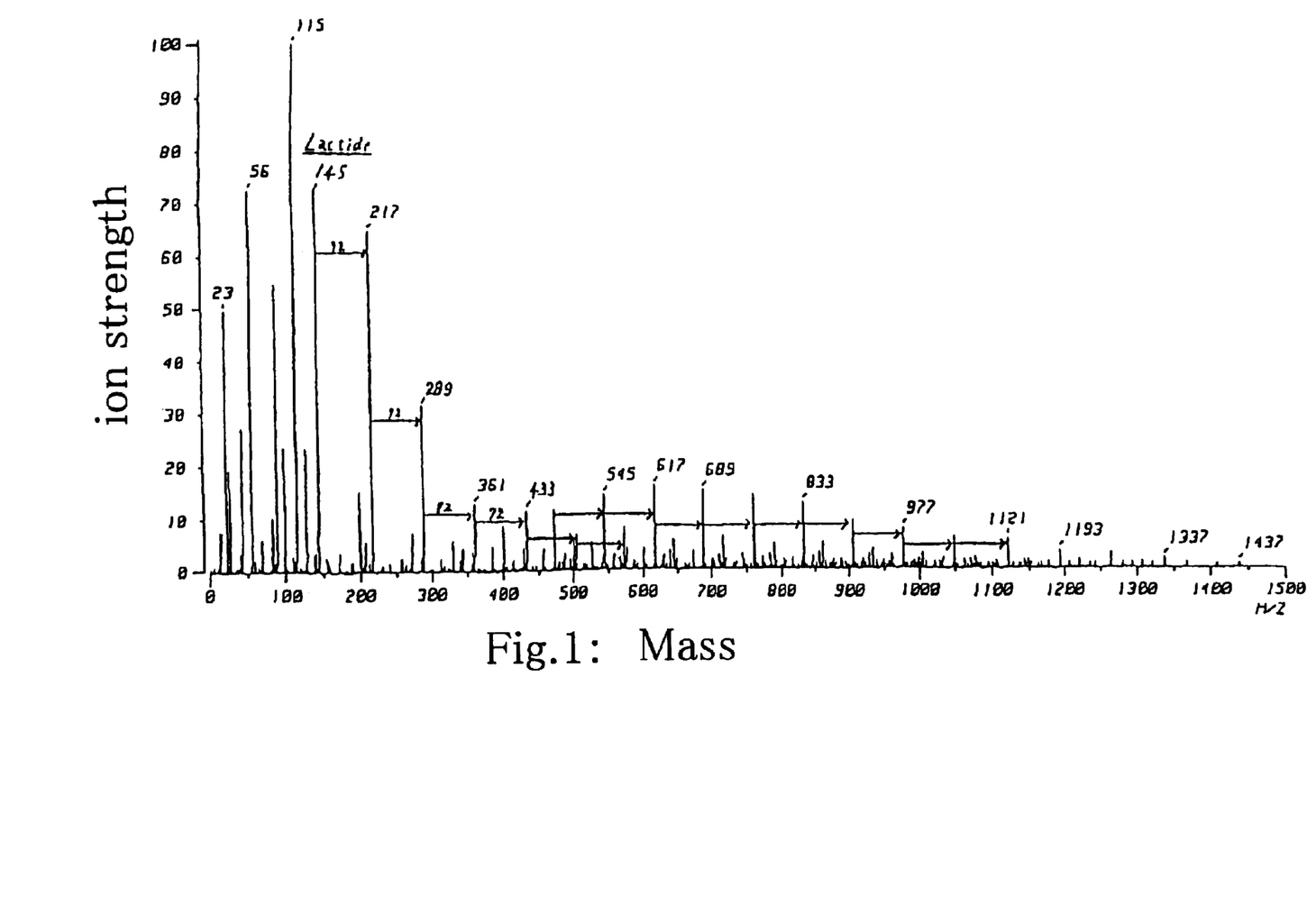
FIG. 1 shows a mass spectrum of the mixture of poly lactic acids obtained by Production Example 1 of the present specification.

The stock solution was placed to a reverse phase ODS column (TSK gel ODS-80 TM) which was previously equilibrated, and was stepwise eluted with 30%, 50% and 100% acetonitrile (pH2.0) each containing 0.01M hydrochloric acid to obtain poly lactic acids (condensation degree of 3 to 19) as an acetonitrile 100% elution fraction. The mass spectrum of the obtained substance is shown in FIG. 1. As is clear from the regular fragment ion peaks in FIG. 1, the obtained mixture of poly lactic acids mainly comprises cyclic condensate, and a small amount of linear condensate is contained therein.

Test Example 1

Evaluation of Action of a Mixture of Poly Lactic Acids Using Diabetes-induced Mice (Method)

Diabetes-induced mice (diabetes mice; C57BL/KsJ-db/db Jcl) were used as test animals. Each of these mice is a homozygote for a recessive gene, db, which exists on the 4th chromosome, and is a diabetes model mouse which rapidly develops type II diabetes by edacity.

These mice (6-week-old female mice obtained from CLEA Japan, Inc.) were divided into two groups: (1) a CE2 group (12 mice), which were fed with standard solid food CE2 (obtained from CLEA Japan, Inc.) and (2) a CPL group (12 mice), which were fed with standard solid food CE2 containing 1 weight % (where a fraction obtained by chromatography is used as is, and the concentration thereof is 1 weight %) of a mixture of poly lactic acids (also referred as to CPL), and then the mice in these groups were fed for 35 days. As a control group, heterozygotes (4 mice; C57BL/KsJ-db/-Jcl) for a recessive gene, db, were fed with standard solid food CE2.

Over the whole period of feeding, fasting blood sugar level, morning blood sugar level, food consumption per day, and body weight were measured.

(Results)

Figure 2:
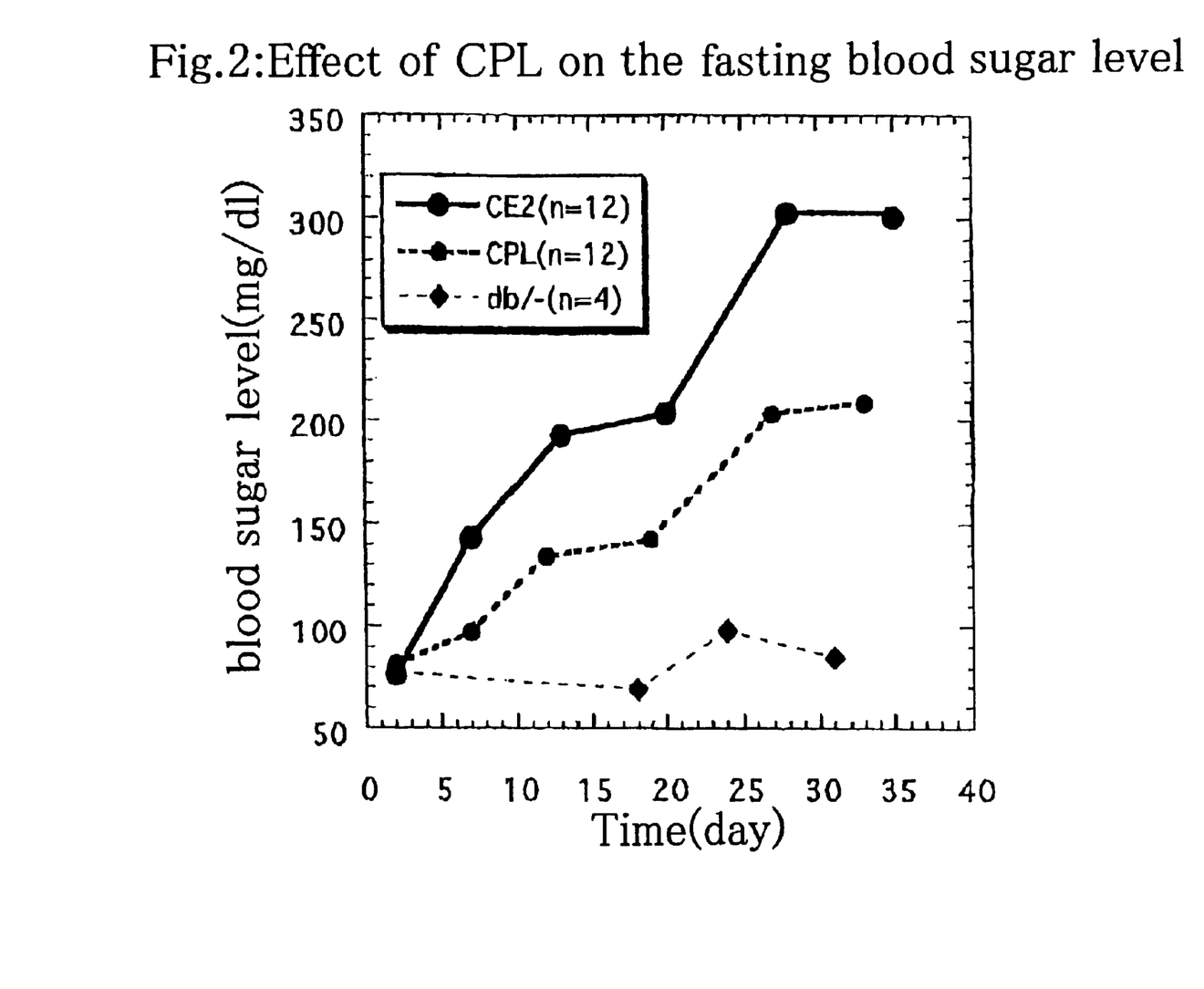
FIG. 2 is a graph showing the effect of the mixture of poly lactic acids on the fasting blood sugar level.
Figure 3:
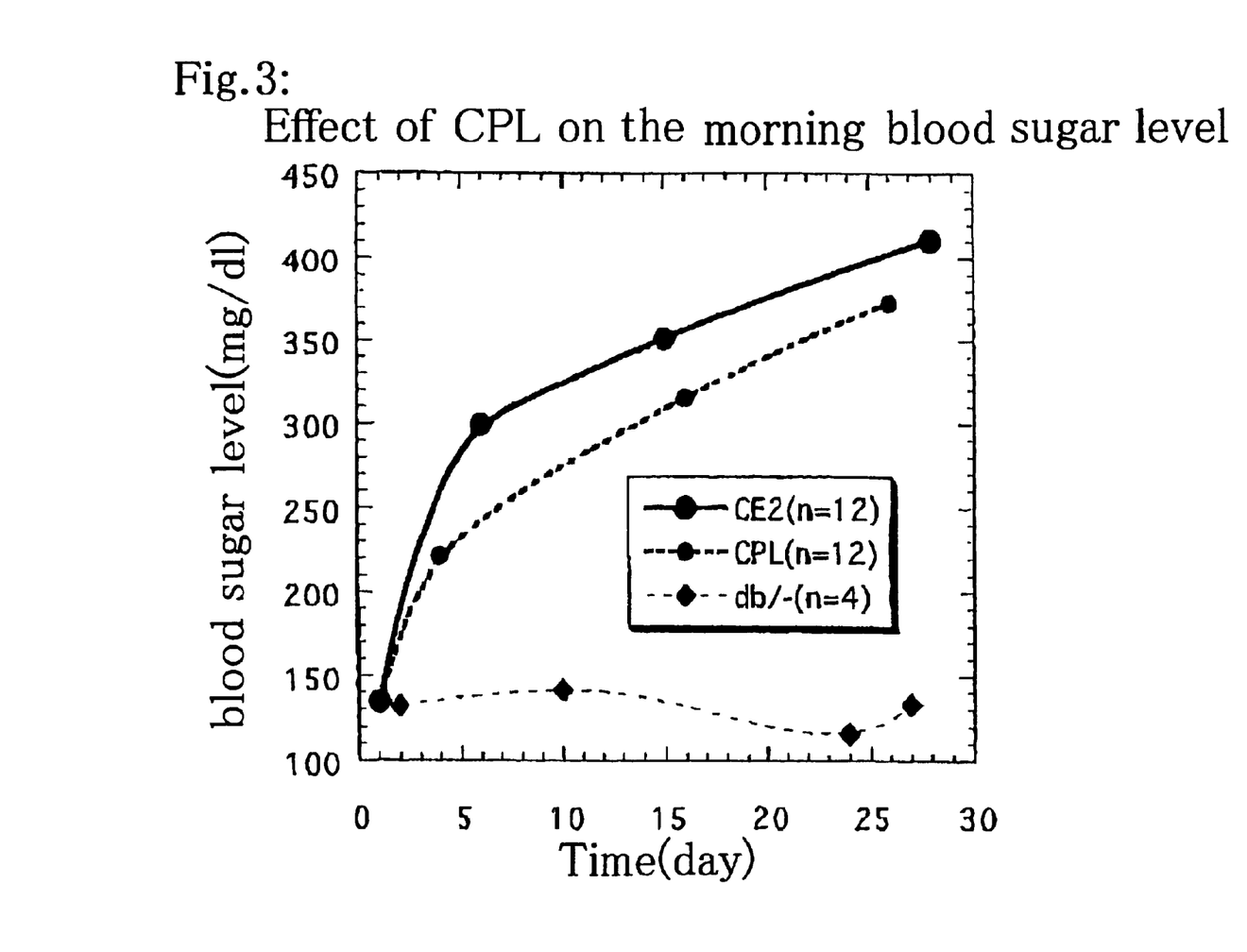
FIG. 3 is a graph showing the effect of the mixture of poly lactic acids on the morning blood sugar level.
Figure 4:
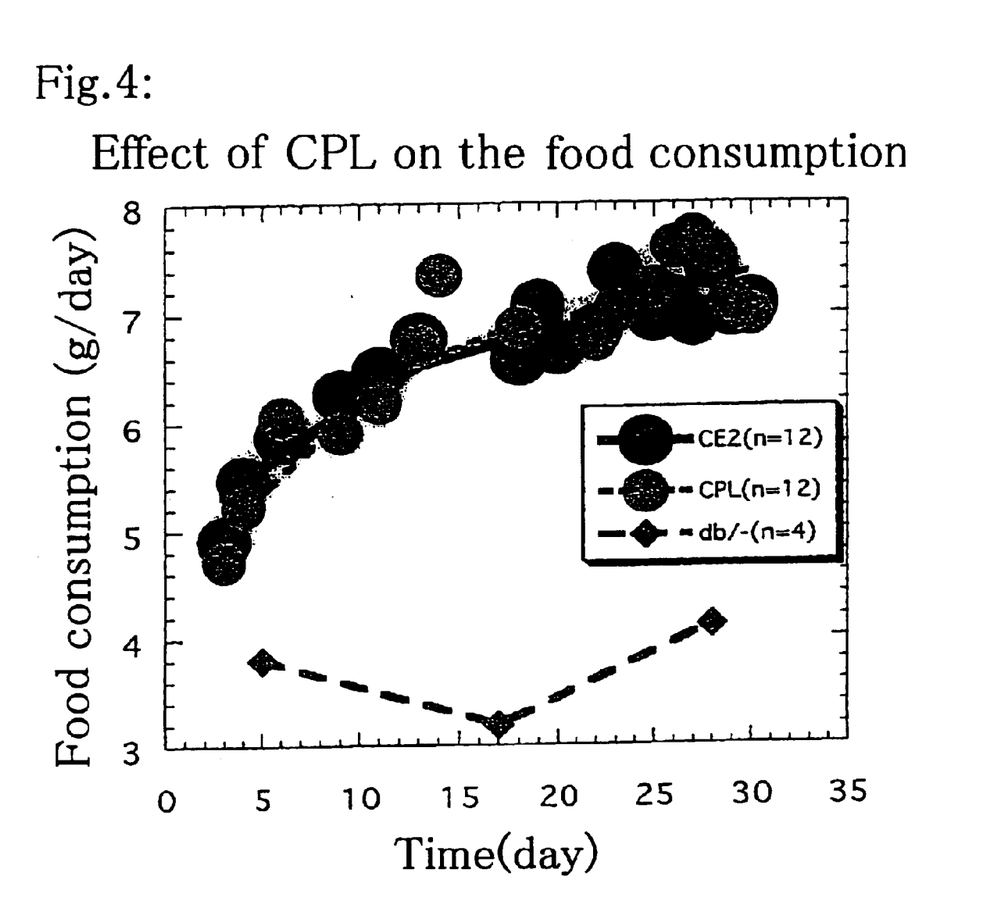
FIG. 4 is a graph showing the effect of the mixture of poly lactic acids on the food consumption.
Figure 5:
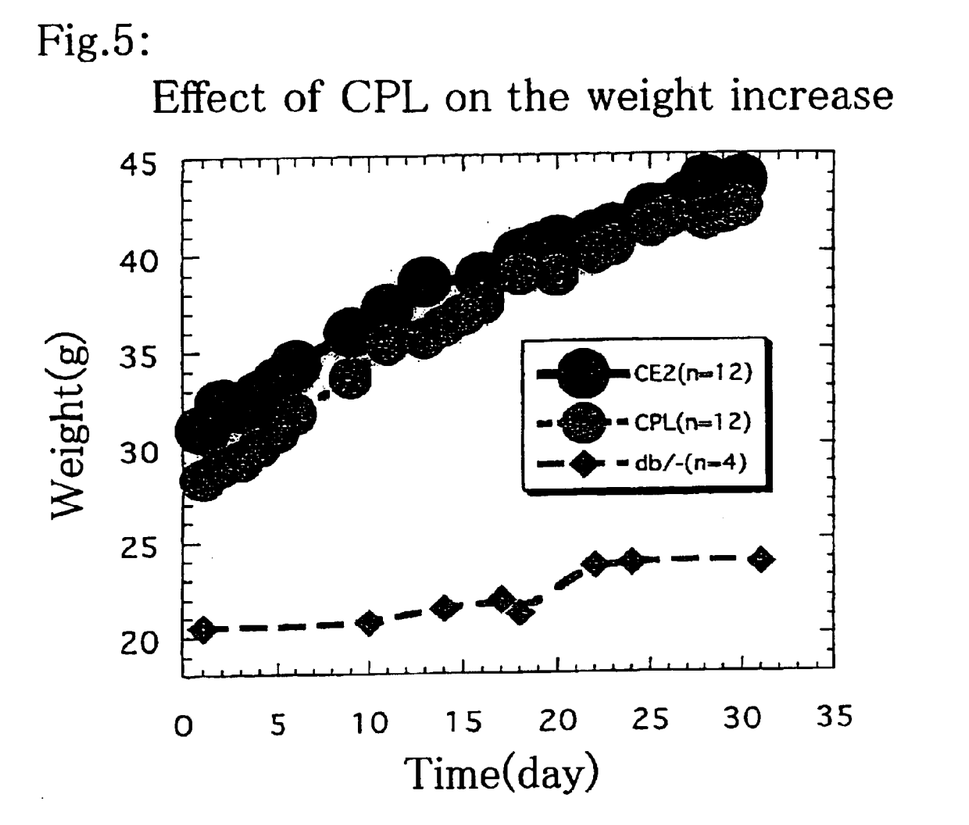
FIG. 5 is a graph showing the effect of the mixture of poly lactic acids on the weight increase.

The results obtained from measurement of fasting blood sugar level are shown in Table 1 and FIG. 2, and the results obtained from measurement of morning blood sugar level, food consumption per day and body weight are shown in FIGS. 3 to 5.

TABLE 1

Results of measurement of fasting blood sugar level
(the unit of values in the table is mg/dl)

| Feeding period (days) | Control group (db/-) | Experiment group (db/db) | |
|---|---|---|---|
| | | Standard solid food group | CPL-containing food group |
| 2 | 77.5 ± 10.4 | 76.2 ± 16.6 | 81.6 ± 16.6 |
| 7 | | 143.0 ± 18.6 | 97.3 ± 17.7 |
| 12 | | | 134.4 ± 19.3 |
| 13 | | 192.8 ± 58.5 | |
| 18 | 69.2 ± 11.2 | | |
| 19 | | | 142.7 ± 26.7 |
| 20 | | 203.6 ± 44.0 | |
| 24 | 98.0 ± 11.0 | | |
| 26 | | | 173.5 ± 37.8 |
| 27 | | | 203.4 ± 45.2 |
| 28 | | 302.7 ± 75.3 | |
| 31 | 84.9 ± 14.2 | | |
| 33 | | | 209.0 ± 46.1 |
| 35 | | 300.9 ± 53.5 | |

As is clear from Table 1 and FIG. 2, the fasting blood sugar level of mice in the IC2 group increased as they grew, and reached 300 mg/dl on the $28^{th}$ day after initiation of feeding. In contrast, the fasting blood sugar level of the CPL group was remarkably lower than that of the CE2 group over the whole feeding period. Especially, the fasting blood sugar level on the $27^{th}$ day after initiation of feeding was about 203 mg/dl on average, and this value was about 67% of the value of CE2 group on the $28^{th}$ day. From these results, it was shown that fasting blood sugar level was significantly reduced by providing a feed containing 1% mixture of poly lactic acids.

Especially, the diabetes model mice used in this test are a model where the blood sugar level is not only difficult to be controlled by diet therapy or kinesitherapy, but is also difficult to be controlled even by administration of insulin. It is a surprising result that the fasting blood sugar level of such a mouse can be reduced to about 67% of a control by providing a feed containing 1% mixture of poly lactic acids. These results suggest the possibility that the blood sugar level of diabetes patients can be controlled by administration of a mixture of poly lactic acids in combination with diet therapy and kinesitherapy.

Moreover, as shown in FIG. 3, there was no significant difference between the CE2 group and the CPL group in respect of morning blood sugar level, and both groups showed similar values.

Furthermore, as shown in FIG. 4, the daily average food consumption of control mice heterozygously having a db gene (C57BL/KsJ-db/-Jcl) was about 4 g, whereas the daily average food consumption of diabetes-induced mice in both CE2 group and CPL group rapidly increased as they grew and reached about 7.5 g on the $29^{th}$ day after initiation of feeding. There was no significant difference between the daily average food consumption of the CE group and that of the CPL group.

Still further, as shown in FIG. 5, in respect of weight increase of growing mice, there was no significant difference between the CE group and the CPL group, and the body weight significantly increased in both groups and reached about 43 g on average on the $29^{th}$ day after initiation of feeding. In contrast, weight increase of control mice (C57BL/KsJ-db/-Jcl) was more moderate than mice in both the CE and CPL groups, and the average body weight on the $31^{st}$ day after initiation of feeding was about 24 g.

INDUSTRIAL APPLICABILITY

The medicament of the present invention has an action of reducing the blood sugar level and is useful especially for prevention and/or treatment of diabetes or diabetes complications. Moreover, since the mixture of poly lactic acids which is used as an active ingredient in the present invention is a low condensed form of lactic acid derived from a biological ingredient, it has a high biocompatibility and has low side effects.

What is claimed is:

1. A method of treating at least one of diabetes and complications arising from diabetes in a subject in need of such treatment, wherein the method comprises administering to the subject a therapeutically effective amount of a mixture of polylactic acids having a condensation degree of 3 to 19.

2. The method of claim 1, wherein the subject is a mammal.

3. The method of claim 2, wherein the mammal is a human.

4. The method of claim 1, wherein the mixture of polylactic acids comprises straight chain polylactic acids.

5. The method of claim 1, wherein the mixture of polylactic acids comprises cyclic polylactic acids.

6. The method of claim 1, wherein the polylactic acids comprise L-lactic acid repeating units.

7. The method of claim 6, wherein the polylactic acids consist essentially of L-lactic acid repeating units.

8. The method of claim 3, wherein the diabetes is type II diabetes.

9. The method of claim 1, wherein the mixture of polylactic acids comprises a fraction obtained by a process which comprises condensing lactic acid by dehydration under an inactive atmosphere, subjecting the ethanol- or methanol-soluble fraction of the obtained reaction solution to reverse phase column chromatography, and eluting with 25 to 50 weight % acetonitrile aqueous solution of pH 2 to 3 and then with 90 weight % or more acetonitrile aqueous solution of pH 2 to 3.

10. The method of claim 9, wherein the dehydration comprises stepwise decompression and temperature rise under nitrogen gas atmosphere.

11. The method of claim 10, wherein the reverse phase column chromatography comprises ODS column chromatography.

12. A method of preventing diabetes in a subject in need thereof, wherein the method comprises administering to the subject an effective amount of a mixture of polylactic acids having a condensation degree of 3 to 19.

13. The method of claim 12, wherein the subject is a mammal.

14. The method of claim 13, wherein the mammal is a human.

15. The method of claim 12, wherein the mixture of polylactic acids comprises straight chain polylactic acids.

16. The method of claim 12, wherein the mixture of polylactic acids comprises cyclic polylactic acids.

17. The method of claim 13, wherein the polylactic acids comprise L-lactic acid repeating units.

18. The method of claim 14, wherein the polylactic acids consist essentially of L-lactic acid repeating units.

19. The method of claim 14, wherein the diabetes is type II diabetes.

20. A method of preventing complications arising from diabetes in a subject in need thereof, wherein the method comprises administering to the subject an effective amount of a mixture of polylactic acids having a condensation degree of 3 to 19.

21. A method of reducing the blood sugar level in a subject, wherein the method comprises administering to the subject an effective amount of a mixture of polylactic acids having a condensation degree of 3 to 19.

22. The method of claim 21, wherein the subject is a human.

23. The method of claim 21, wherein the polylactic acids consist essentially of L-lactic acid repeating units.

24. The method of claim 22, wherein hyperglycemia is treated.

25. The method of claim 24, wherein the hyperglycemia is due to a condition selected from organic disorder of pancreatic tissues, chronic hepatopathy, endocrinopathy, brain hypertension, adiposis, hyperphagia, crapula of alcohol, postgastrectomy, nutritional hyperglycemia, fibrile disease, carbon monoxide poisoning, increase of blood sugar due to drugs, and combinations thereof.

* * * * *